Figure 1:
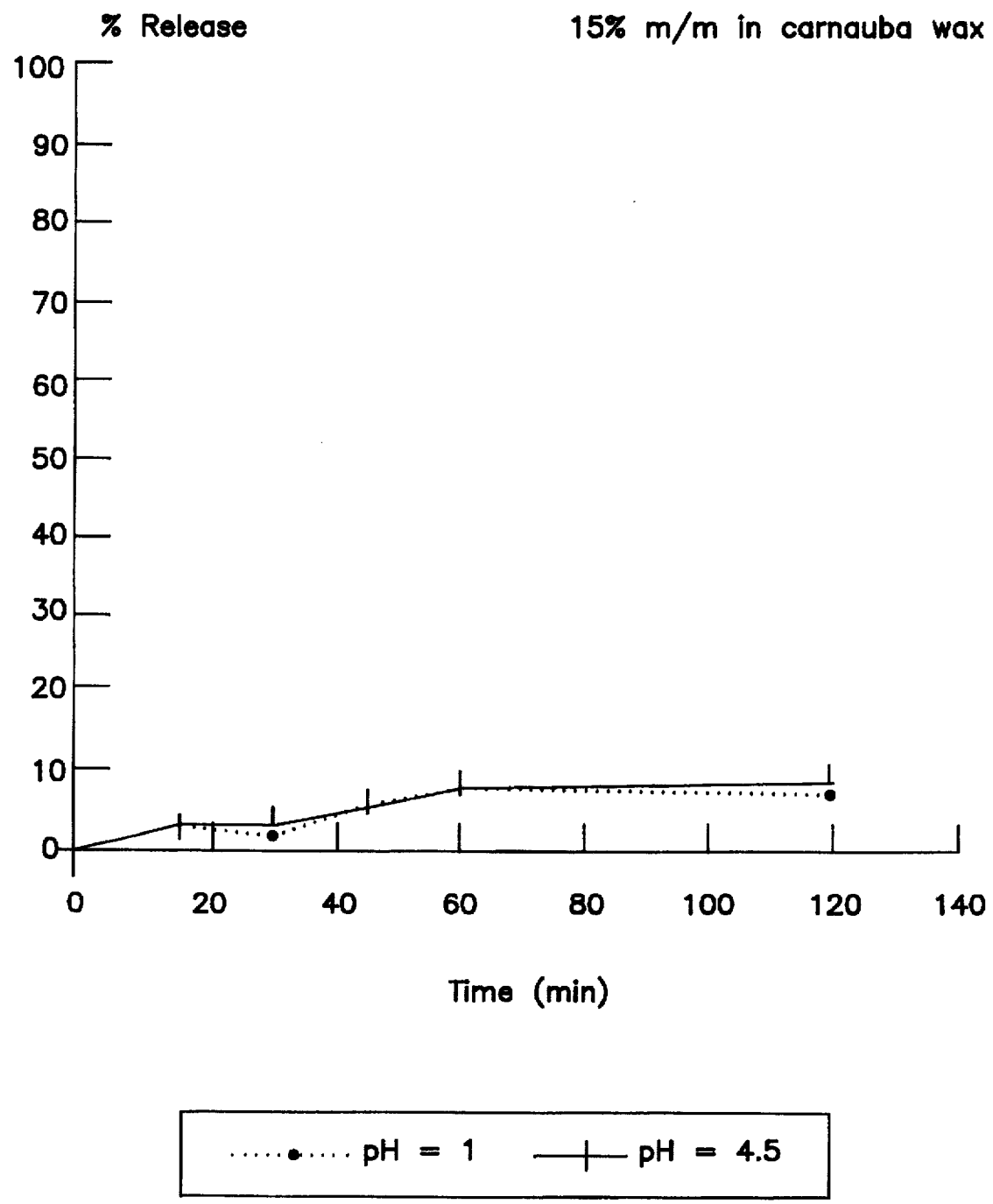
Figures 1, 2A:
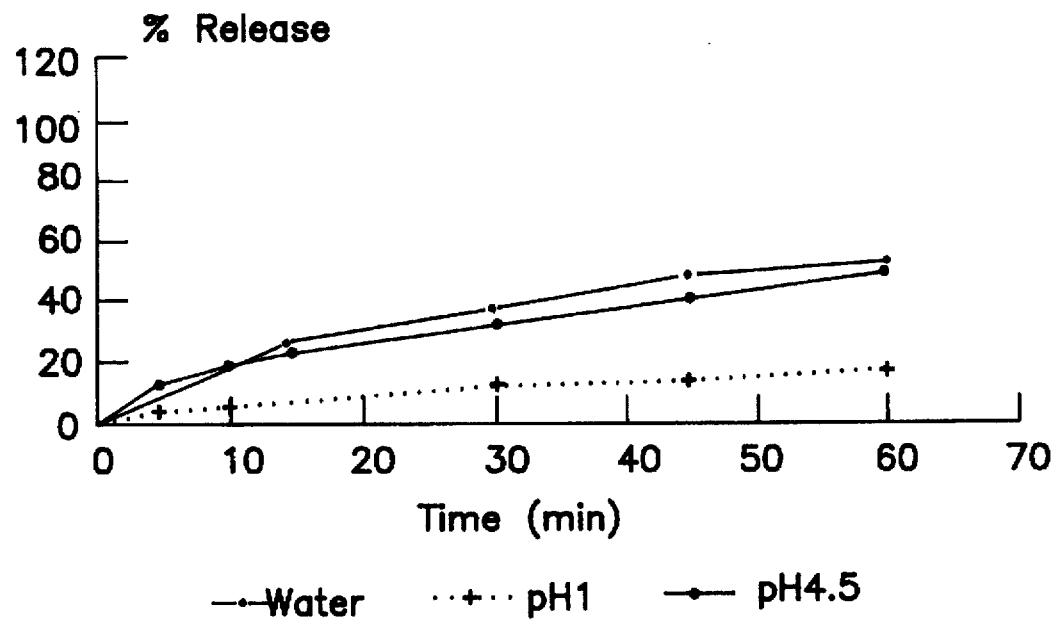
Figures 2, 2A:
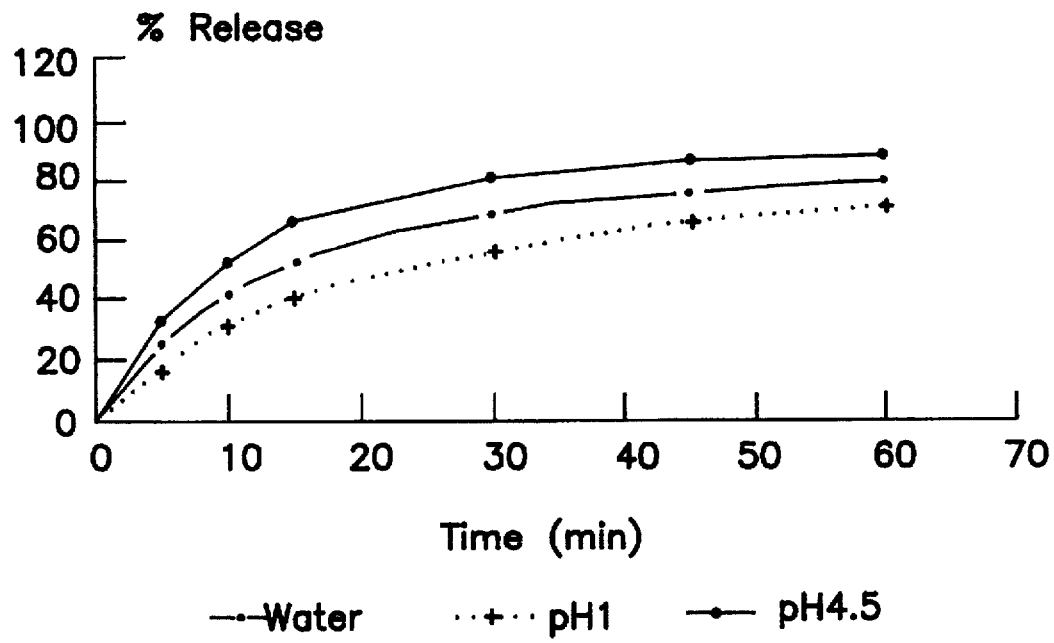
Figures 1, 2B:
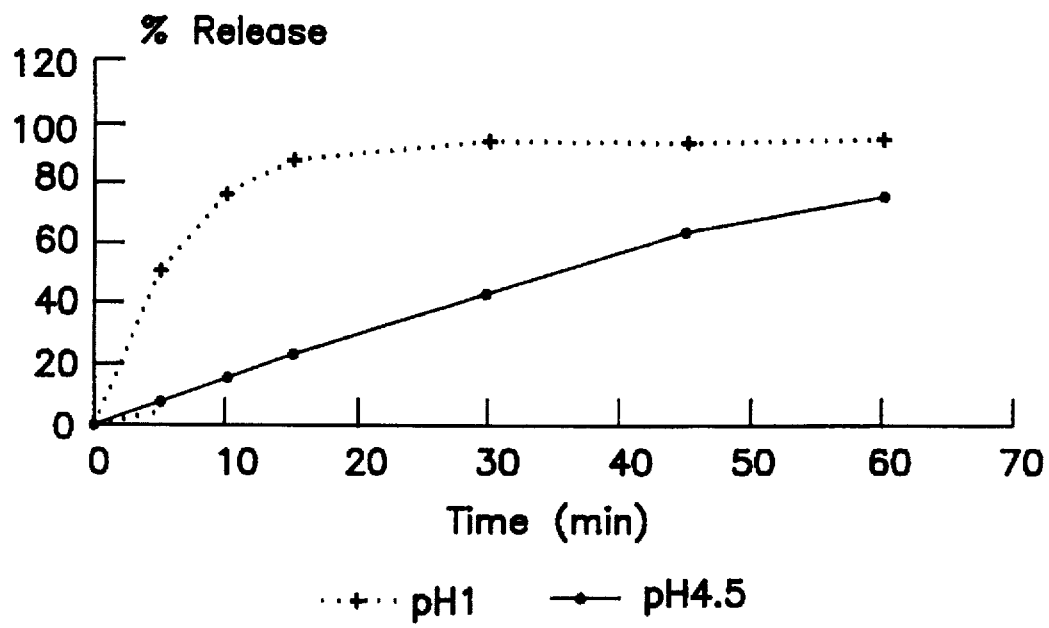
Figures 2, 2B:
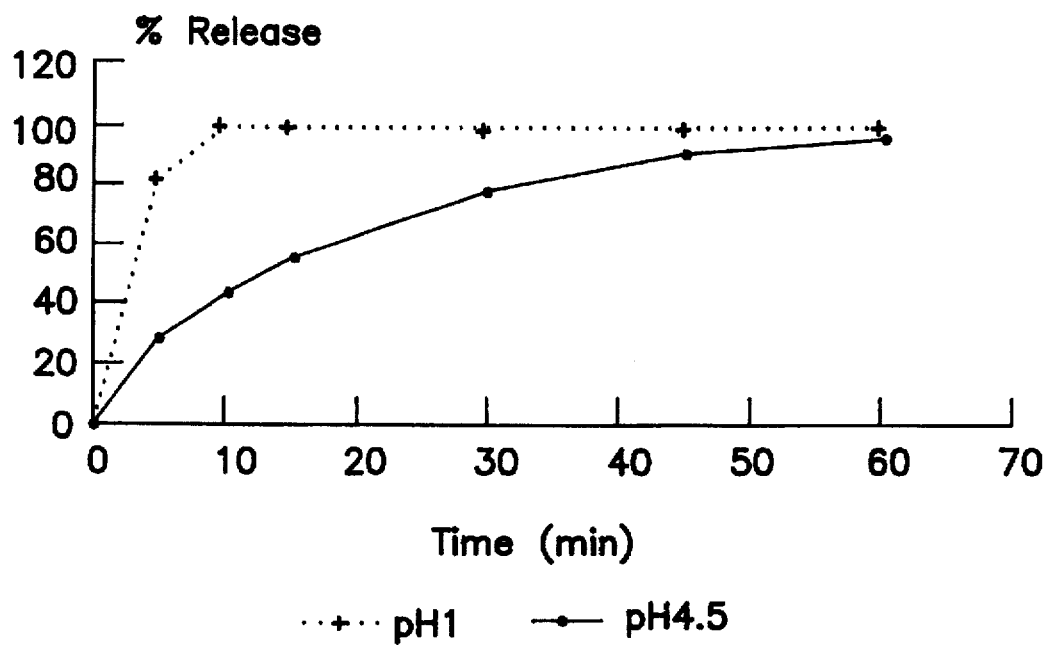
Figures 1, 3A:
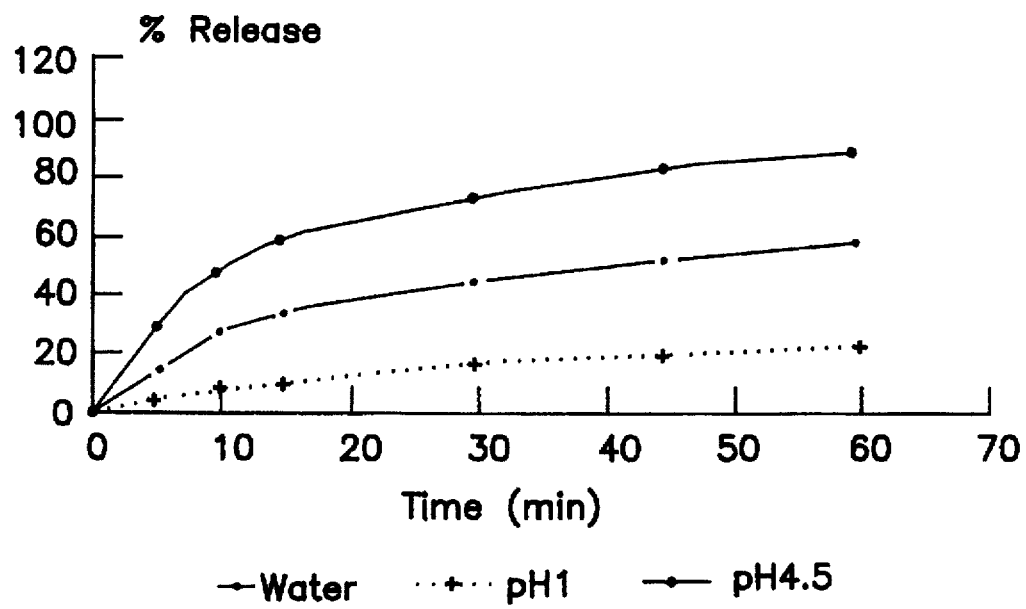
Figures 2, 3A:
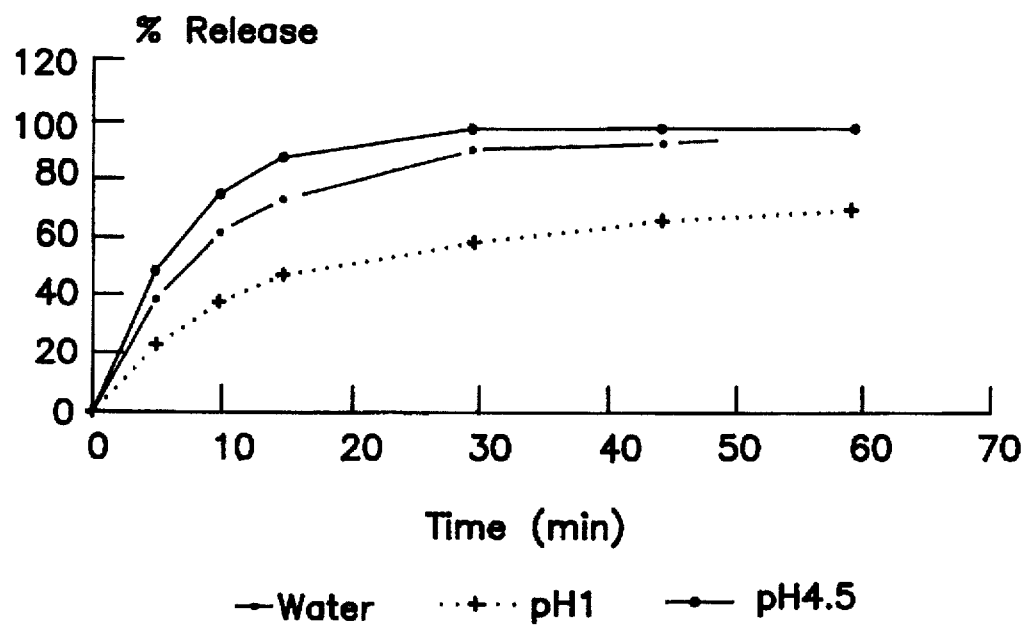
Figures 1, 3B:
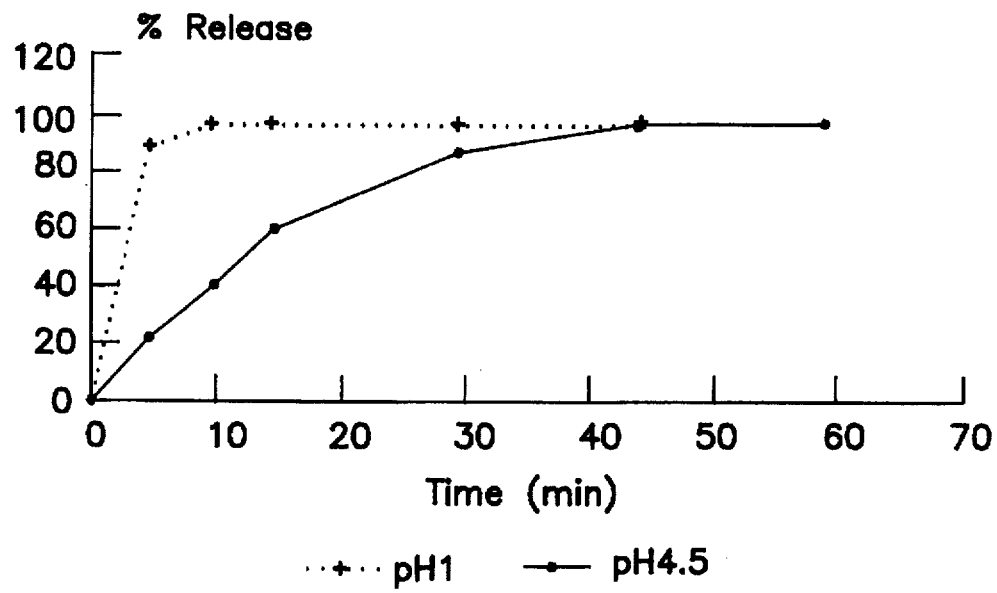
Figures 2, 3B:
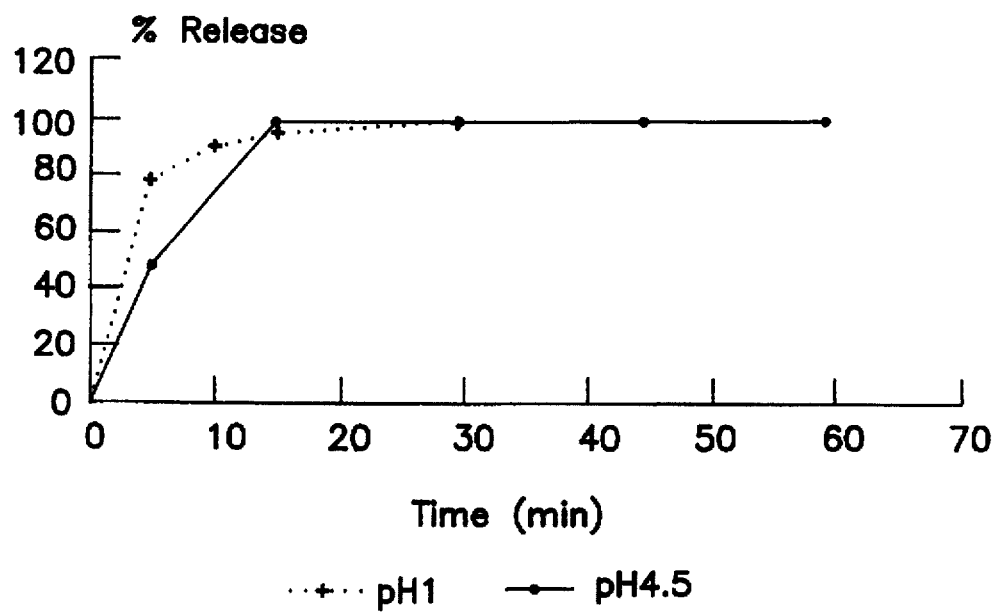
Figure 4A:
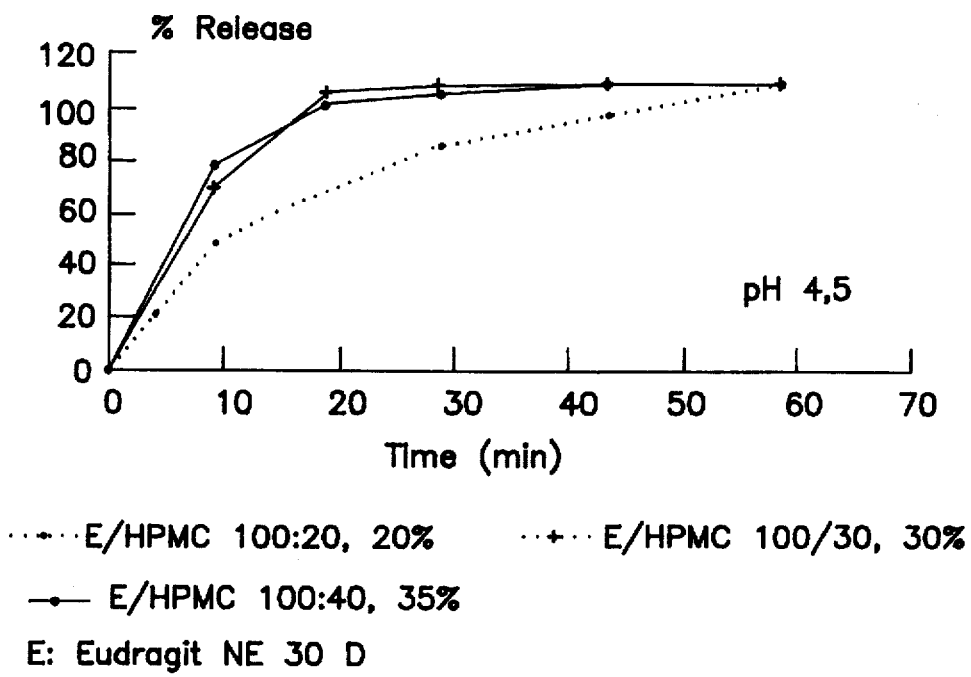
Figure 4B:
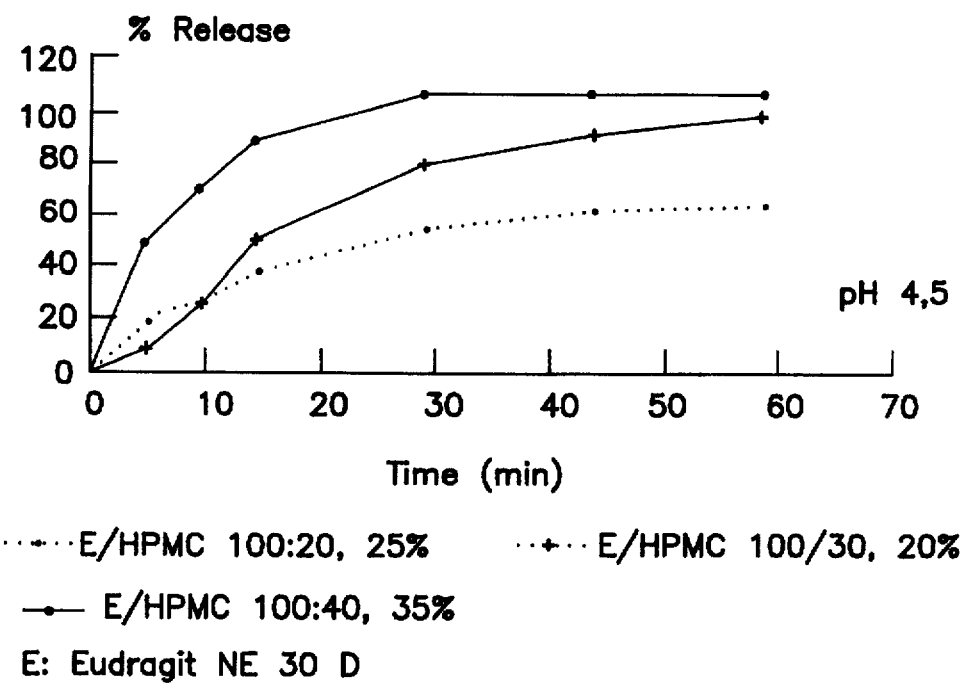
Figures 1, 5A:
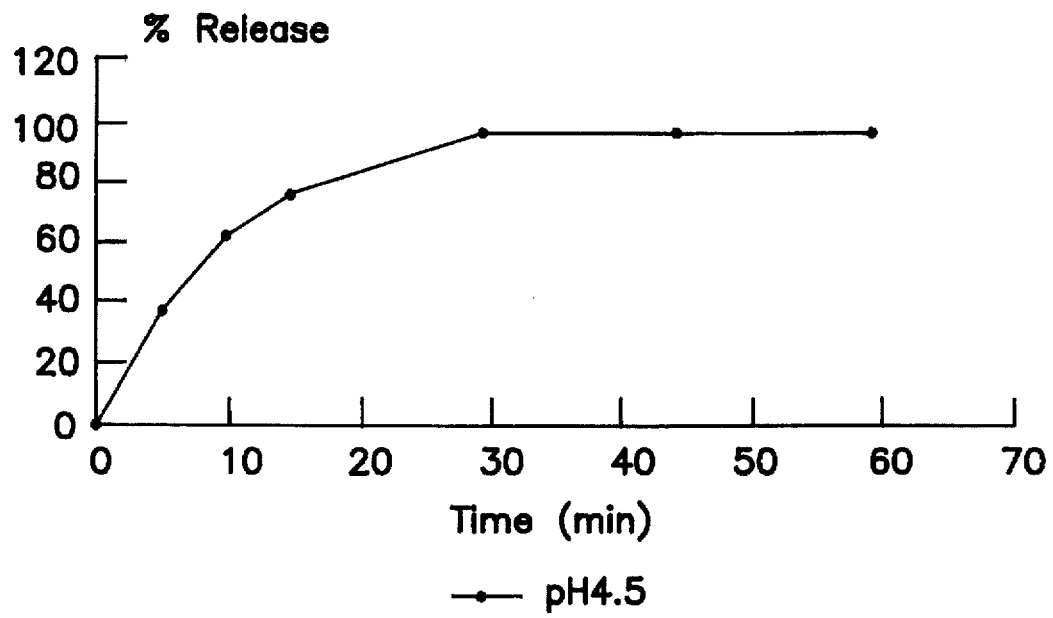
Figures 2, 5A:
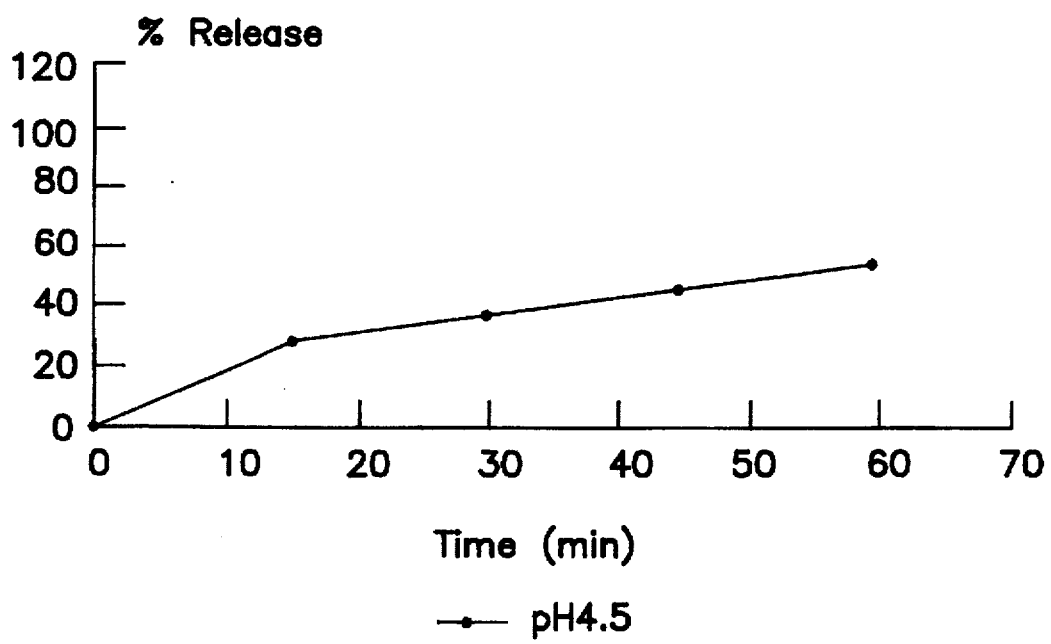
Figures 1, 5B:
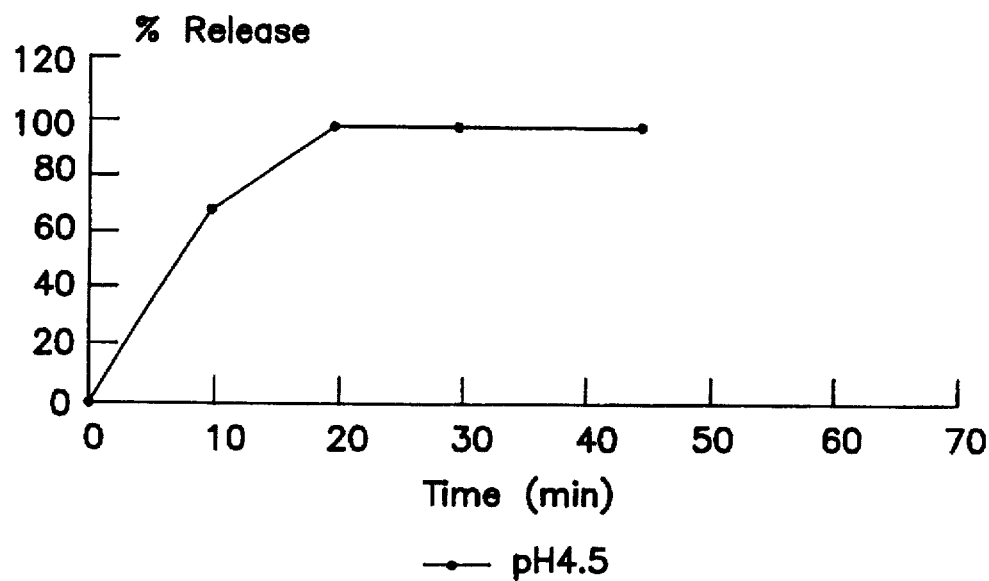
Figures 2, 5B:
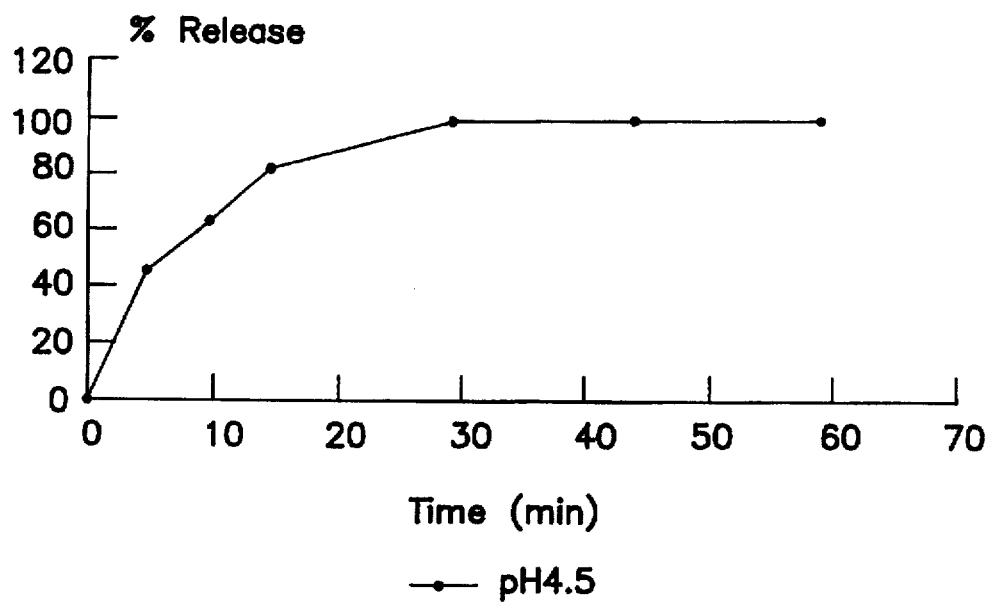

United States Patent [19]
Pöllinger et al.

[11] Patent Number: 5,695,784
[45] Date of Patent: Dec. 9, 1997

[54] FLAVOR-MASKED PHARMACEUTICAL COMPOSITIONS

[75] Inventors: Norbert Pöllinger, Odenthal; Johannes Michaelis, Cologne, both of Germany; Klaus Benke, Kyoto, Japan; Roland Rupp, Leichlingen; Manfred Bücheler, Overath, both of Germany

[73] Assignee: Bayer Aktiengesellschaft, Leverkusen, Germany

[21] Appl. No.: 191,741

[22] Filed: Feb. 4, 1994

Related U.S. Application Data

[63] Continuation of Ser. No. 1,236, Jan. 6, 1993, abandoned.

[30] Foreign Application Priority Data

Jan. 15, 1992 [DE] Germany .............. 42 00 821.2

[51] Int. Cl.⁶ .................................................. A61K 9/62
[52] U.S. Cl. .................. 424/495; 424/489; 424/494; 424/497
[58] Field of Search ..................... 424/489, 494, 424/495, 497; 514/781, 951, 963, 974

[56] References Cited

U.S. PATENT DOCUMENTS

| | | | |
|---|---|---|---|
| 4,764,375 | 8/1988 | Paradissis | 424/153 |
| 4,865,851 | 9/1989 | James et al. | 424/498 |
| 4,931,174 | 6/1990 | Uhlemann et al. | 209/139.1 |
| 4,935,247 | 6/1990 | Marttila et al. | 424/494 |
| 4,946,654 | 8/1990 | Uhlemann et al. | 422/140 |
| 4,971,791 | 11/1990 | Tsau et al. | 424/81 |
| 4,994,260 | 2/1991 | Kallstrand et al. | 424/10 |
| 5,082,669 | 1/1992 | Shirai et al. | 424/495 |

FOREIGN PATENT DOCUMENTS

| | | |
|---|---|---|
| 0101418 | 2/1984 | European Pat. Off. |
| 0189114 | 7/1986 | European Pat. Off. |
| 0273890 | 7/1988 | European Pat. Off. |
| 0295941 | 12/1988 | European Pat. Off. |
| 0312340 | 4/1989 | European Pat. Off. |
| 0409254 | 1/1991 | European Pat. Off. |

OTHER PUBLICATIONS

Esmat E. Zein–El–Dein, Pharm. Ind. 53, 87 (1991).
S. Harder, U. Fuhr, D. Beermann, A.H. Staib, Br. J. Clin. Pharmac. 30, 35 (1990).

*Primary Examiner*—Jyothsna Venkat
*Attorney, Agent, or Firm*—Sprung Horn Kramer & Woods

[57] ABSTRACT

The invention relates to flavour-masked pharmaceutical compositions for oral administration, their preparation and their use as medicaments.

The new pharmaceutical preparations according to the invention make it possible to administer pharmaceutical active substances having very unpleasant organoleptic properties such as, for example, very bad taste, even in liquid form.

1 Claim, 10 Drawing Sheets

| | Parameter | Standard Tablet | Sachet | Difference (%) |
|---|---|---|---|---|
| 5 | AUC (0 -->∞) (mg.h/l) | 8.37; 1.28 | 8.74; 1.21 | +4.4 |
| | AUC norm (kg.h/l) | 1.27; 1.35 | 1.32; 1.30 | +3.9 |
| | C max (mg/l) | 1.70; 1.34 | 1.64; 1.28 | -3.4 |
| 10 | C max.norm (kg/l) | 0.26; 1.36 | 0.25; 1.36 | -3.4 |
| | t max (h) | 2.0 - 4.0 | 1.0 - 4.0 | |
| 15 | t 1/2 (h) | 4.20; 1.18 | 4.25; 1.16 | +1.2 |
| | MRT (h) | 7.12; 1.11 | 6.18; 1.20 | -13.2 |

FIG. 6

| Parameter | Standard Tablet | Oily juice[1] | Difference [%] |
|---|---|---|---|
| AUC (0→∞) [mg·h/l] | 5.35; 1.43 | 5.98; 1.34<br>5.55; 1.24 | + 11.8<br>+ 3.7 |
| AUCnorm [kg·h/l] | 0.77; 1.39 | 0.87; 1.31<br>0.80; 1.24 | + 13.0<br>+ 3.9 |
| Cmax [mg/l] | 1.55; 1.45 | 1.51; 1.36<br>1.53; 1.29 | − 2.6<br>− 1.3 |
| Cmax.norm [kg/l] | 0.22; 1.43 | 0.22; 1.32<br>0.22; 1.28 | ± 0.0<br>± 0.0 |
| tmax (range) [h] | 0.5 − 1.5 | 0.75 − 3.0<br>0.75 − 2.0 | |
| t1/2 [h] | 5.08; 1.20 | 4.60; 1.19<br>4,63; 1.20 | − 9.4<br>− 8.9 |
| MRT [h] | 5.25; 1.15 | 5.48; 1.14<br>5.52; 1.13 | + 4.4<br>+ 5.1 |

[1] upper value: Suspension/freshly prepared
lower value: Suspension/after 14 days at 30°C

FIG. 7

FLAVOR-MASKED PHARMACEUTICAL COMPOSITIONS

This application is a continuation of application Ser. No. 08/001,236, filed Jan. 6, 1993, now abandoned.

The invention relates to flavour-masked pharmaceutical compositions for oral administration, their preparation and their use as medicaments.

The new pharmaceutical preparations according to the invention make it possible to administer pharmaceutical active substances having very unpleasant organoleptic properties such as, for example, very bad taste, even in liquid form.

Especially to elderly people and patients who have difficulty in swallowing, the taking of large-size tablets frequently presents considerable difficulties; large-size tablets are also unsuitable for children.

Solid pharmaceutical forms such as, for example, coated tablets do have the advantage that the patient is not conscious of the possibly unpleasant intrinsic taste of the active ingredient; however, they have the disadvantage that they are not divisible without the flavour-concealing coating being damaged.

An individual dose of the active ingredient, however, in geriatrics and paediatrics is frequently absolutely necessary and can be guaranteed by the provision of a variably meterable granule or juice formulation. The aim underlying the present invention can therefore not be achieved by formulations which have hitherto become known, for example from EP-A-230,811.

It is therefore necessary to provide individually meterable pharmaceutical forms even of unpleasantly tasting active ingredients for oral administration; administration as powders or granules for direct administration would also be advantageous.

The preparation of a liquid pharmaceutical form, for example by breaking up a tablet and dissolving it in water, is not possible without specific taste-concealing measures on account of the extremely bad and long-lasting bitter taste of numerous antimicrobial active ingredients. Due to the extremely unpleasant taste, a significant interference with patient compliance is to be expected. A mere flavouring of active ingredient solutions and suspensions is frequently insufficient even if flavourings are used which are intended specifically to conceal certain types of flavour.

The particularly unpleasantly tasting active ingredients include, from the antimicrobial agents group, the gyrase inhibitors, in particular those of the naphthyridone- and quinolone-carboxylic acid types, very particularly ciprofloxacin, norfloxacin, ofloxacin and enoxacin.

Besides a complete concealment of the taste, a rapid and complete release is unconditionally to be demanded of many active ingredients, in order that a bioavailability equivalent to the tablets can be guaranteed. This is problematic, since for numerous active ingredients there is an absorption window in the upper small intestine and the absorption in the lower intestinal sections is greatly reduced. (S. Harder, U. Fuhr, D. Beermann, A. H. Staib, Br. J. Clin. Pharmac. 30, 35 (1990)). In elderly people, there are also frequently occurring deviations of the gastric pH in the direction of a hypoacidic medium to be taken into account. This means that even in weakly acidic medium—for example at pH 4.5—a rapid dissolution of the active ingredient must be guaranteed.

The object of flavour-masking with simultaneously rapid and complete bioavailability of the active ingredient was achieved by microencapsulation of the active ingredient according to the invention.

Microencapsulation is, per se, a widespread technology which is not only used in pharmacy (P. B. Deasy; Microencapsulation and related Drug Processes; M. Dekker Inc., N.Y. & Basel, 1984).

In the pharmaceutical field, microencapsulation is frequently used if a sustained release of active ingredients is desired. Microcapsules prepared in this way can be administered, for example, intramuscularly; biodegradable polymers are able to control the release of the active substance for days up to weeks and months. For products to be administered orally, microencapsulation with water-insoluble coatings is also a frequently employed method for delaying the release of active ingredient, but also for flavour-masking. Embedding in wax matrices leads, as is known, to flavour-masking. The flavour-masking of bad-tasting medicaments by incorporation into microcapsules based on carnauba wax, beeswax and ethylcellulose or combinations thereof has become known from EP-A-273, 890. The embedding of, for example, ciprofloxacin or ciprofloxacin salts by the method described does not lead, however, to the required rapid release of active ingredient. This type of microencapsulation cannot be used for the desired oral liquid preparation of the pharmaceuticals claimed. (FIG. 1).

EP-A-101,418 describes the microencapsulation of active ingredients using hydrocarbons or hydrocarbon-related substances with the aim of controlled release, flavour-masking and active ingredient stabilisation. With these systems, too, rapid release cannot be achieved. GB-A 2,122,490 describes systems of this type. The release of the active substances takes place with a delay.

One method for masking the flavour of pharmaceuticals, which is based on the preparation of a three-layer coating of medicaments, has become known from DE-A-3,815,562. The coating consists of fat or fat and polymer.

A further flavour-masking method for badly tasting pharmaceuticals, which is likewise based on the use of lipids, has become known from DE-A-3,816,464. U.S. Pat. No. 4,764,375 also describes a method for flavour-masking based on the embedding of the active ingredient in a mixture of lipids.

EP-378,137 describes water-dispersible pharmaceutical preparations which make it possible to administer orally active ingredients having organoleptically unfavourable properties in liquid form. The active ingredient is first applied to sugar spherules which subsequently are provided with a film layer. The medicaments mentioned are relatively low-dose substances such as pinaverium bromide, metoclopramide and salbutamol. The polymers used are water-insoluble substances such as shellac and ethyl-cellulose; they are combined with substances which are soluble below pH 5. The example mentioned is ®Eudragit E 12.5 (Röhm, Darmstadt). The active ingredient should be rapidly released in artificial gastric juice at pH 1.2. For a hypoacidic gastric medium such as, for example, pH 4.5 and a high dose of active ingredient this formulation, however, is unsuitable.

EP-A-212,641 describes flavour-masking compositions, consisting of a pharmaceutical polymer matrix which contains the active ingredient. According to the application the polymer used is a copolymer of methacrylic acid and its methyl ester (®Eudragit S 100). The matrix dissociates in a medium with a pH of less than 4, the active ingredient being released into this medium.

®Eudragit S 100 is used in accordance with the manufacturer's information of Röhm, Darmstadt, for the preparation of gastric juice-resistant, intestinal juice-soluble coatings. A gastric juice-resistant coating is not suitable for the flavour-masking of active ingredients and the rapid and complete release at pH values of 1–4.5 required for this.

The microencapsulation of norfloxacin for the purpose of reducing side-effects such as gastric irritations and haemorrhages is described by Esmat E. Zein-El-Dien (Pharm. Ind. 53, 87 (1991)). The coating material employed is water-soluble methylcellulose; water-insoluble film-forming agents are not mentioned.

The complete flavour-masking combined with a rapid release required for the claimed agents, for example antimicrobial agents, cannot be realised using the methods of the prior art which has hitherto generally become known.

In general, antimicrobially active substances are structures which contain acidic or basic functional groups or, simultaneously, for example, carboxylic acid groups and amines in the molecule (betaines). Customarily, a water-soluble or the best water-soluble form of these active ingredients is employed in order to guarantee a rapid release of active ingredient. With organic carboxylic acids, these are in general their alkali metal or alkaline earth metal salts, and with betaines their carboxylic acid salts or acid salts (for example hydrochlorides).

Surprisingly, it has now been found that the use of the most sparingly water-soluble form of an active ingredient (for example ciprofloxacin) in microcapsules prepared using specific coatings leads to optimum results with respect to flavour-masking and release of active ingredient. In general, in the case of active ingredients which contain carboxylic acid groups, these are the active ingredients themselves and not their salts. In the case of active ingredients which contain basic groups, they are this active form and not its salts. In the case of active ingredients present in betaine form, according to the invention the betaine itself and not a salt is used. This form of the active ingredient is called according to the invention the "base form of the active ingredient". As the starting substance, the active ingredient can optionally either be used in the form of its hydrate or anhydrate; the finished microcapsules contain the active ingredient as anhydrate.

According to the invention, the anhydrates of the active ingredients in the base form in the microcapsules are defined to contain less than 5%, in particular less than 3.0%, of water in the form of water of crystallisation or other water adducts.

The present invention is illustrated below by way of example using the active ingredient ciprofloxacin.

The microcapsules according to the invention are prepared as follows:

The active ingredient is, for example, granulated in moist form in a manner known per se,. it being possible to use water or alcohol/water mixtures, for example ethanol/water mixtures, as granulating auxiliaries. To prepare microgranules by aqueous moist granulation, the hydrate form of the base form of the active ingredient is advantageously employed. If the anhydrate form of the base form of the active ingredient is used to prepare the microgranules, the moist granulation is preferably carried out using alcohol-water mixtures. The moist granules are dried and sieved. The required particle size fraction is incorporated into the subsequent microencapsulation process. Preferred microgranules are prepared by fluidised bed spray granulation as described in EP-A-0,163,836, DE-A-3,808,116 and EP-A-0,332,929. In this process, an aqueous suspension of the active ingredient, which can contain additional auxiliaries in dissolved or suspended form, can be converted directly into a very uniform product composed of spherical active ingredient-auxiliary agglomerates by means of a special method. In each case, the base form of the active ingredient defined above is used for the preparation of these microgranules. In the case of the preparation of the ciprofloxacin microgranules with the aid of the fluidised bed spray granulation method, micronised ciprofloxacin hydrate is likewise advantageously to be employed for the preparation of the spray suspension. It was possible to find that the use of the said grade of active ingredient allowed the preparation of very finely particulate aqueous suspensions without an additional wet-grinding being necessary.

Binders which can be used to increase the mechanical strength of the microgranules are substances such as acacia gum, alginic acid and alginates, carboxymethylcellulose, ethylcellulose, gelatine, hydroxypropylcellulose, hydroxypropylmethylcellulose, methylcellulose, xanthan gum, pectin, tragacanth, microcrystalline cellulose, hydroxyethylcellulose, ethylhydroxyethylcellulose, sodium carboxymethylcellulose, polyethylene glycols, polyvinylpyrrolidone, polyvinyl alcohol, polyacrylic acid, gum arabic, lactose, starch (wheat, maize, potato and rice starch), sucrose, glucose, mannitol, sorbitol, xylitol, stearic acid, hydrogenated cottonseed oil, hydrogenated castor oil, vinylpyrrolidone-vinyl acetate copolymers, fructose, methylhydroxyethylcellulose, agar-agar, carrageenan, karaya gum, chitosan, starch hydrolysates and the like. The use of polyvinylpyrrolidone 25 in a concentration of 1–10%, relative to the microgranules, is particularly advantageous.

The microcapsules according to the invention are prepared by coating the microgranule cores with the coating layer according to the invention in suitable equipment.

A coating is applied to the microgranule cores, which leads to a complete covering of the surface of the granule. In this case, the coating composition of the microencapsulation is to be chosen in a manner such that an adequate permeability for aqueous media and a rapid release of active ingredient is guaranteed. Owing to the composition of the coating and its thickness, it is ensured that the microcapsules are dissolved only after passing through the taste-sensitive region, but the release of active ingredient takes place promptly before passing through the site of absorption. Coatings which lead to gastric juice-resistant coatings and which only permit release of active compound in the intestinal region after passing through the stomach are therefore not suitable.

The use of aqueous coating suspensions is to be preferred for reasons of environmental and occupational safety.

The film-forming agents available per se for the preparation of coatings for the preparation of microcapsules include a number of substances such as acacia gum, acrylic acid polymers and copolymers (polyacrylamides, polyacryldextrans, polyalkyl cyanoacrylates, polymethyl methacrylates), agar-agar, agarose, albumin, alginic acid and alginates, carboxyvinyl polymers, cellulose derivatives such as cellulose acetate, polyamides (nylon 6–10, poly(adipyl-L-lysines, polyterephthalamides and poly(terephthaloyl-L-lysines)), poly-ε-caprolactam, polydimethylsiloxane, polyesters, poly(ethylene-vinyl acetate), polyglycolic acid, polylactic acid and its copolymers, polyglutamic acid, polylysine, polystyrene, shellac, xanthan gum, anionic polymers of methacrylic acid and methacrylic acid esters, to mention only a few.

The application of the coating can be carried out in customary coater equipment such as, for example, a powder-coater working according to the Wurster method. It is advantageous to choose as high as possible a concentration of the coating suspensions in order to make the microencapsulation process as economical as possible.

The compositions according to the invention, however, can only be prepared with microcapsules which are prepared using neutral methyl ester and/or ethyl ester compounds of polymethacrylic acid (®Eudragit NE 30 D, Röhm, Darmstadt) and/or quaternary ammonium compounds of polymethacrylic acid (®Eudragit RL 30 D, ®Eudragit KS 30 D, Röhm, Darmstadt) and ethylcellulose (®Aquacoat, FMC Corp.) as film-forming agents.

These coatings, which are not water-soluble per se, can be combined with water-soluble polymers, which provide for pore formation in the coating, to increase the permeability. Water-soluble pore-forming agents which can be used are substances such as hydroxypropylcellulose, hydroxypropylmethylcellulose, methylcellulose, sodium carboxymethylcellulose, dextran, dextrins, cyclodextrins, polyethylene glycols, polyvinyl alcohols, polyvinylpyrrolidones, starch and starch-hydrolysates such as, for example, modified types of starch (gelatinised starch, STA-RX 1 500, Celutab, maltodextrins), sugars and sugar replacements such as mono-, di- and oligosaccharides, sucrose, fructose, lactose, dextrose, mannitol, sorbitol and xylitol and alginic acid and alginates, tragacanth, pectins, gum arabic and gelatin. Preferred pore-forming agents within the meaning of the invention are hydroxypropylcellulose, hydroxypropylmethylcellulose and methylcellulose.

Preferred coating combinations of water-insoluble and water-soluble components which may be mentioned are mixtures of ®Eudragit NE 30 D with hydroxypropylmethylcellulose. Thus, it was possible with suitable mixtures of these substances, for example in the ratio 100:20 to 100:50, preferably 100:20 to 100:40 and particularly preferably 100:40, to achieve an optimum flavour, concealment and rapid and complete release of the active ingredient from microcapsules in the pH range from 1 to 4.5.

Even other coatings expressly recommended for flavour-masking in the specialist literature such as, for example, cationic copolymer of dimethylaminoethyl methacrylate and neutral methacrylic acid esters (®Eudragit E 12.5), did not lead to the desired results with respect to flavour-masking and release behaviour. Thus, in view of EP-A-378,137, the use of ®Eudragit E 12.5 could appear to be indicated for flavour-masking. Surprisingly, however, it was found that, for example, the combination of ®Eudragit NE 30 D with HPMC led to the best flavour-masking with simultaneously good release of active ingredient at pH 1 and 4.5.

Furthermore, for film formation the addition of a plasticiser can be necessary. In this case, these are substances which facilitate film formation and increase the elasticity and mechanical stability of the coating.

Plasticisers which can be employed are substances such as, for example, diethyl phthalate, acetyl tributylcitrate, glycerol, diethyl sebacate, dimethyl phthalate, dibutyl phthalate, tributyl citrate, butyl stearate, polyethylene glycols of different chain lengths, glycerol monostearate, triacetin, castor oil and other native and synthetic oils, triethyl citrate, acetyl triethylcitrate, 1,2-propylene glycol, acetylated fatty acid glycerides and polyoxyethylene-polyoxypropylene copolymers.

The incorporation of surface-active substances into the coating shell assists, on the one hand, the spreading of the coating dispersion on the solid particles during the microencapsulation process and leads, on the other hand, to an improved wettability of the microcapsules. It can furthermore contribute to an effect on the coating permeability.

The wetting agents which can be employed are substances such as sodium laurylsulphate (USP), polysorbate (20, 40, 60, 80, 65, 61, 85 and 21), poloxamers (ethylene oxidepropylene oxide block copolymers) of differing HLBs, lecithins, oleic acid and oleic acid salts, sorbitan esters (Span 20, 40, 60, 80 and 85), propylene glycol monostearate and monolaurate, glycerol monostearate and monooleate, Brij types (fatty alcohol-PEG ethers) of differing HLBs (for example PEG 10 cetyl ether, PEG 20 oleyl ether etc.), Myrj types (fatty acid-PEG esters) of differing HLBs (for example PEG 40 monostearate; PEG 100 monostearate and the like), sodium dodecylsulphate (SDS), dioctyl sodium sulphosuccinate (DOSS), ethoxylated mono- and diglycerides of differing HLBs (Tagat types), sucrose fatty acid esters, fatty acid salts (Na, K, Ca, Mg, Al etc.), ethoxylated triglycerides (polyoxyethylated castor oil (40), polyoxyethylated hydrogenated castor oil (40 and 60), polyoxyethylated vegetable oils), sterols (cholesterol and wool wax alcohols) in concentrations of 0.001–20%, preferably 0.1–2%.

In order to decrease or to avoid completely the adhesion or the agglutination of particles during the microencapsulation process, antiadhesive agents should be added. Suitable substances are, for example, magnesium stearate, calcium stearate, calcium behenate, talc, colloidal silicic acid, stearic acid, Precirol (mixture of mono-, di- and triesters of palmitic and stearic acid with glycerol), hydrogenated cottonseed oil, hydrogenated castor oil and polyethylene glycol of differing molecular weights.

Amounts of 0.1–90%, particularly of 5–40%, are preferably employed.

Colorants can additionally be present in the coating shell.

The microcapsules can be provided with a polishing layer. This serves not only for visual improvements, but also represents an important functional unit of the microcapsules according to the invention. By applying a final layer over the actual coating a direct interaction of, for example, an oily juice component with the flavour-concealing coating is prevented. In particular when using a water-soluble or at least hydrophilic polishing layer, direct contact of an oily juice excipient with the microcapsule coating shell and a delay in release caused by oil/coating interactions can be prevented. In addition, the tendency of microcapsules to stick when introduced into an aqueous liquid is reduced.

Suitable polishing agents are polyethylene glycols of differing molecular weight or mixtures thereof, talc, surfactants (Brij types, Myrj types, glycerol monostearate and poloxamers), fatty alcohols (stearyl alcohol, cetyl alcohol, lauryl alcohol and myristyl alcohol and mixtures thereof). Preferably, polyethylene glycols having molecular weights of 3,000–20,000 are employed.

The polishing agent is applied following the coating of the microgranules. The polishing agents can be worked either in solid or dissolved form.

The size of the microcapsules is of great importance for the good acceptance of the liquid oral pharmaceutical form prepared therefrom. If the microcapsules administered are too large, a subjective "feeling of sand" in the mouth cannot be excluded. A particle size which is too large can moreover lead to increased sedimentation of the microcapsules in the dispersion medium. For this reason, a size of the microcapsules of 10–1,000 µm, preferably of 10–800 µm and very particularly preferably of 100–500µm is to be desired.

The microcapsules according to the invention described here lead on the one hand to an excellent flavour-masking and on the other hand to the very rapid release of active ingredient demanded for pharmacokinetic reasons. Within 15–30 min, at least 70–80% of the encapsulated active ingredient can be brought into solution. This requirement is fulfilled in the in vitro test both for strongly acidic (pH 1) and weakly acidic (pH 4.5) pH media. This result represents the excellent bioavailability of the active ingredient formulated according to the invention.

Surprisingly, it was found that a complete flavour-masking and the rapid release of active ingredient demanded to guarantee a high bioavailability is achievable if the active ingredient (for example ciprofloxacin) is microencapsulated with the auxiliaries according to the invention, the active ingredient substance to be employed is preferably the betaine form (base form of the active ingredient).

besides a complete flavour-masking a rapid release of active ingredient is guaranteed if the base form of the active ingredient (for example ciprofloxacin betaine) is employed for microencapsulation. A rapid solubility can be guaranteed when using a suitable coating recipe and coating application amount both in the strongly acidic and in the weakly acidic medium (pH 1 and 4.5). On the other hand, the flavour-masking of active ingredients which are employed in the form of a soluble salt of the base form of the active ingredient cannot be achieved with the coating amounts which suffice for the flavour-masking of the base form of the active ingredient. The release of, for example, ciprofloxacin HCl from microcapsules is furthermore delayed.

the rapid release of the active ingredient present in the base form can be guaranteed if a special coating is used which contains both water-insoluble or swellable components and water-soluble components in a suitable ratio.

It has furthermore been found that the use of the anhydrate form of the base form of the active ingredient is particularly suitable to guarantee a sufficiently rapid release of the active ingredient from microcapsules both in the strongly acidic and in the weakly acidic medium. A control of the release of active ingredient by means of the moisture content of the microcapsules is thus possible: on the one hand it can be guaranteed that the microcapsules remain "tight" over a desired period and thus the flavour-concealing is provided. However, it is also ensured that, after a variable time, the active ingredient can be released from the microcapsules and absorbed.

The use of the microcapsules according to the invention is particularly essential if a juice formulation, for example based on an oily juice base, is to be prepared with it which should meet the release requirements described in the strongly acidic or weakly acidic release medium (FIGS. 2–5).

The bioavailability of two representative formulations according to the invention corresponds to that of a rapid-release tablet formulation (FIG. 6–7).

A rapid release of active ingredient can also be achieved in accordance with the prior art by the use of a disintegrant. A disadvantage in comparison to disintegrant-free recipes, however, is that considerably higher amounts of coating have to be applied to microcapsule cores containing disintegrant and the unpleasant-tasting active ingredient in order to guarantee a flavour-concealing microencapsulation at all. This leads to a prolongation of the microencapsulation process period and an increase in costs.

The invention also relates to the control of the release rate by means of the moisture content of the microcapsules: by adjustment of the water content, for example of the ciprofloxacin microcapsules to the anhydrate stage of the base form of the active ingredient, a considerable increase in release can be effected, which renders superfluous the use of a customary disintegrant unfavourable for the economy of the process.

The moisture content of the microcapsules can be adjusted in varying ways: Thus, the microgranules to be coated can be adjusted to a desired moisture content before the coating process and optionally subjected to an additional after-drying to the anhydrate stage after the coating operations.

Microgranules which are coated without special predrying and can initially have a water content of up to 30% by weight can be adjusted to the required water content (anhydrate stage of the base form of the active ingredient) by drying after the microencapsulation process.

The microcapsules obtained according to the invention can be further formulated to give medicaments. Possible administration forms are, for example, juice or sachet.

1. Juice based on oil (multiple dose form)

The provision of an aqueous finished juice formulation is not possible, since the coating shell of the microcapsules becomes permeable in aqueous medium after some time. It is therefore advantageous to select a non-aqueous dispersion medium for the microcapsules.

Suitable oily dispersion media are those such as almond oil, arachis oil, olive oil, poppy-seed oil, ground-nut oil, cottonseed oil, soyabean oil, maize oil, ethyl oleate, oleyl oleate, isopropyl myristate and isopropyl palmitate. Medium chain triglycerides are particularly suitable on account of their neutral flavour and their favourable viscosity.

Liquid auxiliaries which can be combined with the said oily carriers and which can be used are ethanol, glycerol, propylene glycol, polyethylene glycol, 1,3-butanol, benzyl alcohol, diethylene glycol and triethylene glycol and the like.

Further additives which are advantageously employed are wetting agents. Oily juice formulations are sensitive to moisture. Even small amounts of water lead to significant viscosity increases which can make a controlled discharge of the originally liquid pharmaceutical form from the container more difficult or impossible. Emulsifiers, on the one hand, increase the water tolerance of an oily formulation and, on the other hand, facilitate the wettability of the microcapsules during incorporation into the oily excipient liquid. They furthermore decrease the viscosity of oily suspensions. Wetting agents which can be used are the substances already described.

The processing of lecithin in concentrations of 0.01 to 20% is particularly advantageous and very particularly advantageous in concentrations of 0.1–10%, preferably of 0.5–5%, relative to a juice formulation.

Furthermore, combinations of lecithin with W/O emulsifiers such as, for example, sorbitan fatty acid ester types, fatty alcohols and glycerol mono- and di-fatty acid esters are particularly suitable to reduce the sensitivity of oily juices, which besides active ingredient microcapsules contain relatively large amounts of sugars or sugar substitutes, to water.

Density-increasing and thus suspension-stabilising additives which are suitable are preferably sucrose, mannitol, sorbitol, xylitol, fructose, glucose, lactose and other sugars and sugar substitutes. The concentration in the oily juice is 5–70%, preferably 15–60%, very particularly 20–40%. These substances must be present in the oily juice in a very fine particle size (mean particle size about 1–50 µm, particularly preferably 3–20 µm). This is achieved by either employing milled substances or homogenising the oily suspension base by wet-grinding.

Surprisingly, it has been found that the best physical stability for oily suspension juices can be achieved when using sucrose.

Antioxidants used to protect oily excipient media are substances such as α-, β-, γ- and δ-tocopherol, ascorbyl palmitate, ascorbyl stearate, L-cysteine, thiodipropionic acid, thiolactic acid, thioglycolic acid, monothioglycerol, propyl gallate, butylhydroxyanisole, butylhydroxytoluene and the like.

Antimicrobial auxiliaries which can be employed are phenol, cresol (o-, p- and m-), p-chloro-m-cresol, benzyl alcohol, phenylethyl alcohol, phenoxyethyl alcohol, chlorobutanol, methyl, ethyl, propyl or butyl p-hydroxybenzoates, benzalkoniumchloride and other quaternary ammonium compounds, chlorhexidine diacetate and digluconate, phenylmercury compounds, thiomersal, benzoic acid and its salts, sorbic acid and its salts, ethanol, 1,2-propylene glycol, glycerol, 2-bromo-2-nitro-propane-1, 3-diol, cetrimide and 2,4,4'-trichloro-2'-hydroxydiphenyl ether in a suitable concentration.

To increase the stability to sedimentation, viscosity-increasing substances such as colloidal silicic acid, bentonite etc. can furthermore be used.

Flavourings, sweeteners and colorants can furthermore be added.

The containers into which the suspensions are filled can consist, for example, of glass or of plastic. At the same time, the container materials can contain substances which impart a particular type of protection, for example protection against light, to the contents.

The composition of the microcapsules employed for an oily juice formulation, in particular the grade of active ingredient and its hydration state and the film composition and coating application amount, are of crucial importance for the quality of a preparation of this type. The rapid release of active ingredient demanded can surprisingly be obtained if the base form of the active ingredient is present in the microcapsules suspended in the oily juice as anhydrate; in contrast corresponding recipes with microcapsules which have a higher water content, for example at the level of the dihydrate stage, give an unacceptable, too slow release of active ingredient.

It has furthermore been found that, for example for ciprofloxacin oily juices, those microcapsules are very suitable which contain ®Eudragit 12.5, ®Eudragit RL 30, ®Eudragit RS 30 D and/or ethylcellulose and e.g. HPMC and also magnesiumstearate or talcum as coating components; particularly suitable, however, are microcapsules which contain a mixture of ®Eudragit NE 30 D and HPMC and also magnesium stearate as coating components; using these coating compositions it was surprisingly possible to prepare a stable oily juice formulation with respect to flavour-masking of the microencapsulated medicaments. As a very particularly preferred coating composition with respect to flavour-masking and release properties, recipes containing ®Eudragit NE 30 D and HPMC in the ratio 100 to 20–50 parts by weight with the addition of magnesium stearate and Tween 20 can be mentioned (FIGS. 4 and 5); a ratio of 100 to 40 parts by weight is particularly preferred.

An oil-based juice formulation can be prepared in a different form: as a finished juice or as an "oily inspissated juice".

An oily finished juice consists of the juice components mentioned in what has gone before and the microencapsulated active ingredient suspended therein. The stability of the formulation must be guaranteed for several years. The release of active ingredient, in particular, must not undergo any significant changes even during storage times of several years.

An "oily inspissated juice" is understood as being a formulation which consists of an oily placebo juice and the separately packaged microcapsules. The user prepares the administrable pharmaceutical form before use by adding the separately packaged microcapsules to the oily placebo juice.

Stability is to be separately guaranteed both for the placebo juice and for the microcapsules, which are present packed separately. Furthermore, the stability of the pharmaceutical oily juice which is ready for administration prepared therefrom over the application period of, for example, 5–15 days is necessary. The composition of the "oily inspissated juice" prepared is as a rule identical to that of the finished juice.

Packaging means for the separately packaged microcapsules which can be used are, for example, glass bottles, bags of suitable plastic films or metal foils. The bag material must be impermeable to water or water vapour in order that the stability of the anhydrate form of the active ingredient contained in the microcapsules is ensured.

2. Sachet (individual dose form)

A further pharmaceutical form which contains active ingredient microcapsules and which can be mentioned are powders or granules.

The active ingredient microcapsules are filled into powder bags (sachets) together with suitable auxiliaries, introduced by the patient into a suitable amount of liquid, preferably water, and the mixture is then drunk.

In this case, attention is to be paid to the fact that an undesired release of active ingredient does not already take place in the dispersion medium and the bitter taste of the dissolved active ingredient appears gain. This requirement can be achieved by the selection of a suitable microcapsule composition.

Preferred film-forming agents which can be used are neutral methyl and ethyl ester compounds of polymethacrylic acid (®Eudragit NE 30 D, Röhm, Darmstadt) together with hydroxypropylmethylcellulose, magnesium stearate and Tween 20, furthermore quaternary ammonium compounds of polymethacrylic acid (®Eudragit RL 30 D, ®Eudragit RS 30 D, Röhm, Darmstadt) in combination with triethyl citrate and talc and also ethylcellulose and hydroxypropylmethylcellulose with triacetin. Preferred coating combinations contain mixtures of 100 parts by weight of ®Eudragit RL 30 D and/or ®Eudragit RS 30 D and 5 to 30 parts by weight of triethyl citrate. Very particularly preferred coatings are comprising mixtures of ®Eudragit NE 30 D with HPMC, e.g. in a ratio of 100:20 to 100:50, preferably 100:20 to 100:40, particularly preferably 100:40, combined with magnesium stearate and Tween 20. Suitable microcapsules are mentioned by way of example in the present working Examples 15–25 and 28–29.

Since the microcapsules are suspended in the aqueous medium, a physical stabilisation of the suspension is necessary. For this reason, density-increasing substances such as sucrose, mannitol, sorbitol, xylitol, fructose, glucose and other customary sugars or sugar replacements are used in amounts of 1–5 g per sachet.

Viscosity-increasing and sedimentation-delaying auxiliaries which can be employed are acacia gum, agar-agar, agarose, alginic acid and alginates, hydroxypropylcellulose, hydroxypropylmethylcellulose, methylcellulose, sodium carboxymethylcellulose, dextran, polyethylene glycol, polyvinyl alcohol, polyvinylpyrrolidone, starch and xanthan gum. The concentrations of the polymers are between 0.01 and 1.0 g, preferably between 0.1 and 0.8 g per sachet of 5–6 g total weight. It is very important that the viscosity-increasing substance dissolves rapidly in cold water and does not lead to lump formation.

In order to enable the patient to stir a sachet into water without problems, wetting agents are added in concentrations of 0.0001–0.1 g per sachet. Suitable substances have been already mentioned above. The polysorbates are particularly suitable.

To optimise the outward appearance of the sachet suspension in water, water-insoluble substances such as microcrystalline cellulose, titanium dioxide and colorants can be added.

Flavouring is carried out by addition of flavours and sweeteners such as, for example, sodium cyclamate, saccharin or aspartame. Since the addition of flavourings can cause a shift in the pH of aqueous suspensions to the acidic range and an undesired release of active ingredient can thus occur, buffering to the pH range from 7–8 is to be carried out.

For this purpose, phosphate buffer according to Sorensen, citric acid/phosphate buffer according to McIlvaine, Britton-Robinson buffer, tetraethylenediamine buffer, trismaleate buffer, dimethylaminoethylamine buffer, triethanolamine HCl buffer, N-dimethylaminoleucylglycine-NaOH buffer, tris-HCl buffer and the like can be used.

The sachets can be prepared by simple physical mixing of the microcapsules containing active ingredient with the necessary auxiliaries or by means of granulation, for example fluidised bed granulation.

Primary packaging means which can be used for the sachets to be mentioned as an individual dose form are preferably glass bottles, bags of suitable plastic films or metal foils. The bag material must be impermeable to water and water vapour in order that the stability of the anhydrate form of the active ingredient contained in the microcapsules is ensured.

Compositons of microgranules containing the active ingredient in betaine form for the preparation of microcapsules

| | Example | | |
|---|---|---|---|
| | 1 according to the invention with PVP 25 | 2 according to the invention without PVP 25 | 3 Comparison Example with disintegrant |
| Ciprofloxacin (betaine) | 10.00 | 10.00 | 10.00 |
| PVP 25 | 0.70 | — | 0.70 |
| Ac-Di-Sol | — | — | 1.00 |
| | 10.70 | 10.00 | 11.70 |
| Preparation | Moist granulation Fluidised bed spray granulation | Moist granulation — | Moist granulation Fluidised bed spray granulation |

Composition of microcapsules containing the active ingredient in hydrochloride form with ® Eudragit NE 30 D/HPMC coatings (Comparison examples)

| | Example | | |
|---|---|---|---|
| | 4 | 5 | 6 |
| ® Eudragit NE 30 D/HPMC or ME = | 100:10 | 100:20 | 100:20 |
| Coating application amount (theoret.) | 40% | 15% | 40% |
| Ciprofloxacin HCl | 1470.00 | 1470.00 | 1470.00 |
| PVP 25 | 30.0 | 30.0 | 30.0 |
| ® Eudragit NE 30 D (dry substance) | 469.2 | 159.4 | 425.2 |
| HPMC 3 cp | — | 32.0 | 85.3 |
| Tylose MH 300 | 46.8 | — | — |
| Magnesium stearate | 84.0 | 32.0 | 85.3 |
| Tween 20 | 4.2 | 1.6 | 4.2 |

Compositon of microcapsules containing the active ingredient in hydrochloride form with ® Eudragit NE 30 D/HPMC coatings (Comparison examples)

| | Example | | | | |
|---|---|---|---|---|---|
| | 7 | 8 | 9 | 10 | 11 |
| ® Eudragit NE 30 D/HPMC or MC = | 100:30 | 100:30 | 100:40 | 100:40 | 100:40 |
| Coating application amount (theoret.) | 20% | 30% | 50% | 60% | 80% |
| Ciprofloxacin HCl | 1470.00 | 1470.00 | 1470.00 | 1470.00 | 1470.00 |
| PVP 25 | 30.0 | 30.0 | 30.0 | 30.0 | 30.0 |
| ® Eudragit NE 30 D (dry substance) | 201.9 | 302.9 | 468.75 | 562.5 | 750.0 |
| HPMC 3 cp | 60.7 | 91.0 | 187.50 | 225.0 | 300.0 |
| Magnesium stearate | 35.4 | 53.1 | 93.75 | 112.5 | 150.0 |
| Tween 20 | 2.1 | 3.1 | 5.25 | 6.3 | 8.4 |

Composition of microcapsules containing the active ingredient in hydrochloride form with ® Eudragit NE 30 D/HPMC coatings (Comparison examples)

| | Example | |
|---|---|---|
| | 12 | 13 |
| ® Eudragit RL 30 D/triethyl citrate = | 100:10 | 100:20 |
| Coating application amount (theoret.) | 50% | 60% |
| Ciprofloxacin HCl | 1470.00 | 1470.00 |
| Maize starch, moist | 30.00 | 30.00 |
| ® Eudragit RL 30 D (dry substance) | 387.55 | 442.80 |
| Triethyl citrate | 39.00 | 88.65 |
| Talc | 323.25 | 368.55 |

Composition of microcapsules containing the active ingredient in hydrochloride form with ® Eudragit E 12.5 (Comparison examples)

| | Example 14 |
|---|---|
| Coating application amount (theoret.) | 50% |
| Ciprofloxacin HCl | 1470.00 |
| Maize starch, moist | 30.00 |
| ® Eudragit E 12.5 (dry substance) | 409.50 |
| Microcrystalline cellulose | 170.25 |
| Magnesium stearate | 170.25 |

Composition of microcapsules containing the active ingredient in betaine form with ® Eudragit NE 30 D/HPMC coatings

| | Example | | | | |
|---|---|---|---|---|---|
| | 15 | 16 | 17 | 18 | 19 |
| ® Eudragit NE 30 D/HPMC = | 100:10 | 100:20 | 100:20 | 100:20 | 100:30 |
| Coating application amount (theoret.) | 20% | 15% | 20% | 25% | 20% |
| Ciprofloxacin | 10.000 | 10.000 | 10.000 | 10.000 | 10.000 |
| PVP 25 | 0.700 | 0.700 | 0.700 | 0.700 | 0.700 |
| ® Eudragit NE 30 D (dry substance) | 1.660 | 1.138 | 1.517 | 1.897 | 1.440 |
| HPMC 3 cp | 0.167 | 0.228 | 0.304 | 0.380 | 0.432 |
| Magnesium stearate | 0.298 | 0.228 | 0.304 | 0.380 | 0.252 |
| Tween 20 | 0.015 | 0.012 | 0.015 | 0.019 | 0.015 |

Composition of microcapsules containing the active ingredient in betaine form with ® Eudragit NE 30 D/HPMC coatings

| | Example | | | | |
|---|---|---|---|---|---|
| | 20 | 21 | 22 | 23 | 24 |
| ® Eudragit NE 30 D/HPMC = | 100:40 | 100:40 | 100:40 | 100:40 | 100:40 |
| Coating application amount (theoret.) | 20% | 35% | 40% | 50% | 60% |
| Ciprofloxacin | 10.000 | 10.000 | 10.000 | 10.000 | 10.000 |

-continued

| | | | | | |
|---|---|---|---|---|---|
| PVP 25 | 0.700 | 0.700 | 0.700 | 0.700 | 0.700 |
| ® Eudragit NE 30 D (dry substance) | 1.328 | 2.324 | 2.656 | 0.320 | 3.984 |
| HPMC 3 cp | 0.531 | 0.929 | 1.062 | 1.328 | 1.593 |
| Magnesium stearate | 0.265 | 0.464 | 0.530 | 0.662 | 0.795 |
| Tween 20 | 0.015 | 0.026 | 0.030 | 0.038 | 0.045 |

Composition of microcapsules containing the active ingredient in betaine from with ® Eudragit NE 30 D/HPMC coatings and polishing layer

| | Example 25 |
|---|---|
| ® Eudragit NE 30 D/HPMC = | 100:40 |
| Coating application amount (theoret.) | 20% |
| Ciprofloxacin HCl | 10.000 |
| Maize starch, moist | 0.700 |
| ® Eudragit E 12.5 (dry substance) | 1.328 |
| HPMC 3 cp | 0.531 |
| Magnesium stearate | 0.265 |
| Tween 20 | 0.015 |
| PEG 6000 | 0.642 |

Compositon of microcapsules containing the active ingredient in betaine form with ® Eudragit NE 30 D/HPMC coatings (Comparison examples with addition of disintegrant)

| | Example | |
|---|---|---|
| | 26 | 27 |
| ® Eudragit NE 30 D/HPMC = | 100:30 | 100:30 |
| Coating application amount (theoret.) | 60% | 60% |
| Ciprofloxacin | 10.000 | 10.000 |
| PVP 25 | 0.700 | 0.700 |
| Ac-Di-Sol | 1.000 | 1.000 |
| ® Eudragit NE 30 D (dry substance) | 4.725 | 4.725 |
| HPMC 3 cp | 1.419 | 1.419 |
| Magnesium stearate | 0.828 | 0.828 |
| Tween 20 | 0.048 | 0.048 |
| PEG 6000 | — | 0.936 |

Composition of microcapsules containing the active ingredient in betaine form with ® Eudragit RL 30 D coatings

| | Example | |
|---|---|---|
| | 28 | 29 |
| ® Eudragit RL 30 D/triethyl citrate = | 100:20 | 100:10 |
| Coating application amount (theoret.) | 50% | 60% |
| Ciprofloxacin | 10.000 | 10.000 |
| PVP 25 | 0.700 | 0.700 |
| ® Eudragit RL 30 D (dry substance) | 2.638 | 3.320 |
| Talc, sieved | 2.188 | 2.760 |
| Triethyl citrate | 0.525 | 0.340 |

Composition of microcapsules containing the active ingredient in betaine form with ® Eudragit RL 30 D coatings (Comparison examples with addition of disintegrant)

| | Example | |
|---|---|---|
| | 30 | 31 |
| ® Eudragit RL 30 D/triethyl citrate = | 100:20 | 100:20 |
| Coating application amount (theoret.) | 60% | 60% |
| Ciprofloxacin | 10.000 | 10.000 |
| PVP 25 | 0.700 | 0.700 |
| Ac-Di-Sol | 1.000 | 1.000 |
| ® Eudragit RL 30 D (dry substance) | 3.460 | 3.460 |

-continued

| | | |
|---|---|---|
| Talc, sieved | 2.870 | 2.870 |
| Triethyl citrate | 0.690 | 0.690 |
| PEG 6000 | — | 0.936 |

Examples 32–34

| Ciprofloxacin sachets 500 mg | No. 32 | No. 33 |
|---|---|---|
| Ciprofloxacin | 500.000 | 500.000 |
| Polyvinylpyrrolidone 25 | 35.000 | 35.000 |
| ® Eudragit NE 30 D | 161.200 | 166.000 |
| HPMC 3 cp | 65.000 | 66.400 |
| Magnesium stearate | 32.500 | 33.200 |
| Tween 20 | 1.300 | 1.900 |
| Mannitol | 4050.000 | 4000.000 |
| Avicel pH 101 | 400.000 | 400.000 |
| Titanium dioxide | 40.000 | 40.000 |
| HPC-H fine | 50.000 | 100.000 |
| Citric acid monohydrate | 5.000 | 5.000 |
| Disodium hydrogenphosphate dihydrate | 80.000 | 80.000 |
| Polyvinylpyrrolidone 25 | 200.000 | 200.000 |
| Tween 20 | 5.000 | 5.000 |
| Oragne flavour | 275.000 | 275.000 |
| | 5900.000 | 5907.500 |
| ® Eudragit NE 30 D/HPM = 100:40; Coating application | 48.6% | 50% |

Example 34
Ciprofloxacin microcapsules in an oily juice formulation
(Instructions for the preparation of 140 ml of ciprofloxacin juice 5% m/v)

| | |
|---|---|
| Ciprofloxacin | 7.000 |
| Polyvinylpyrrolidone 25 | 0.490 |
| ® Eudragit NE 30 D | 2.257 |
| HPMC 3 cp | 0.910 |
| Magnesium stearate | 0.455 |
| Tween 20 | 0.018 |
| Miglyol 812 | 98.214 |
| Sucrose, microfine | 39.025 |
| Lipoid S 75 | 1.405 |
| Strawberry flavour | 0.156 |

Microcapsules:
® Eudragit NE 30 D/HPMC = 100:40; coating application 48.6%.

We claim:

1. A pharmaceutical composition containing an active ingredient which is flavour-masked by microcapsulation having a rapid release of an active ingredient and high bioavailability characterized in that the active ingredient is ciprofloxicin and is present as the anhydrate of its base form and contains less than 5% of water in the form of water of crystallization or other water adducts and is present in an oily juice formulation and the capsule walls consist of a coating which comprises a cationic copolymer of dimethylaminoethyl methacrylate and neutral methyacrylic acid esters, neutral methyl ester and/or ethyl ester compounds of polymethacrylic acid; quaternary ammonium compounds of polymethacrylic acid, or ethylcellulose and triethylcitrate and optionally hydroxypropylmethylcellulose and the microcapsules have a size of 10 to 800 µm.

* * * * *